United States Patent
Goldstein et al.

(10) Patent No.: US 12,217,600 B2
(45) Date of Patent: Feb. 4, 2025

(54) DESIGNER CONTROL DEVICES

(71) Applicant: The Diablo Canyon Collective LLC, Wilmington, DE (US)

(72) Inventors: Steven Wayne Goldstein, Delray Beach, FL (US); John Usher, Beer (GB)

(73) Assignee: The Diablo Canyon Collective LLC, Wilmington, DE (US)

( * ) Notice: Subject to any disclaimer, the term of this patent is extended or adjusted under 35 U.S.C. 154(b) by 249 days.

(21) Appl. No.: 17/068,416

(22) Filed: Oct. 12, 2020

(65) Prior Publication Data

US 2021/0027617 A1    Jan. 28, 2021

Related U.S. Application Data

(63) Continuation of application No. 14/335,902, filed on Jul. 19, 2014, now abandoned, which is a
(Continued)

(51) Int. Cl.
*G08C 17/02* (2006.01)
*A61B 5/00* (2006.01)
(Continued)

(52) U.S. Cl.
CPC ............ *G08C 17/02* (2013.01); *A61B 5/6817* (2013.01); *G06F 3/041* (2013.01); *A61B 5/0022* (2013.01); *A61B 5/0205* (2013.01)

(58) Field of Classification Search
CPC ..... G08C 17/02; A61B 5/6817; A61B 5/0022; A61B 5/0205; A61B 5/024;
(Continued)

(56) References Cited

U.S. PATENT DOCUMENTS 3,876,843 A     4/1975   Moen
4,054,749 A    10/1977   Suzuki et al.
(Continued)

FOREIGN PATENT DOCUMENTS

| EP | 1519625 A2 | 3/2005 | |
|---|---|---|---|
| JP | 2007279020 A * | 10/2007 | ........... A44C 5/0015 |
| RU | 2315635 C2 * | 1/2008 | ........... A61B 5/0002 |
| WO | 2006037156 A1 | 4/2006 | |
| WO | WO-2008022271 A2 * | 2/2008 | ............. H04S 1/005 |

(Continued)

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.
(Continued)

*Primary Examiner* — Brian A Zimmerman
*Assistant Examiner* — Anthony D Afrifa-Kyei
(74) *Attorney, Agent, or Firm* — Aikin & Gallant, LLP

(57) ABSTRACT

A control device configurable to couple to one or more devices having different control functions and a method of facilitating remote control of at least one device having different control functions includes a processor that receives an instruction for at least one of the control functions and additional information from the at least one device, the processor including a plurality of processing algorithms, the additional information received from the at least one device including at least a locally transmitted data signal. The processor selectably processes the additional information using at least one of the processing algorithms and controls a touch sensitive display reconfigurable for the different control functions, such that the at least one control function and the selectably processed additional information are presented on the touch sensitive display. The processor also generates at least one control signal responsive to receiving
(Continued)

the locally transmitted data signal. Other embodiments are disclosed.

20 Claims, 8 Drawing Sheets

Related U.S. Application Data continuation of application No. 12/111,005, filed on Apr. 28, 2008, now Pat. No. 8,788,077.

(60) Provisional application No. 60/914,319, filed on Apr. 27, 2007.

(51) Int. Cl.
  *G06F 3/041* (2006.01)
  *A61B 5/0205* (2006.01)

(58) Field of Classification Search
  CPC ....... A61B 5/02438; A61B 5/332; A61B 5/00; A61B 5/02; A61B 5/0245; A61B 5/318; A61B 5/361; A61B 5/486; A61B 5/681; A61B 5/742; A61B 2560/0266; A61B 2560/0468; A61B 5/339; G06F 3/041; G06F 3/0484; G06F 9/451; G06F 1/163; G06F 21/32; G06F 3/015; G06F 3/016; G06F 3/017; G06F 3/0346; G06F 3/0414; G06F 3/048; G06F 3/04847; G06F 3/0485; G06F 9/453; G06T 13/80; G16H 10/60; G16H 40/63; G16H 50/20; G16H 50/30; G16H 70/20; H04W 4/30
  See application file for complete search history.

(56) References Cited

U.S. PATENT DOCUMENTS

| | | |
|---|---|---|
| 4,088,849 A | 5/1978 | Usami et al. |
| 4,947,440 A | 8/1990 | Bateman et al. |
| 5,208,867 A | 5/1993 | Stites, III |
| 5,267,321 A | 11/1993 | Langberg |
| 5,524,056 A | 6/1996 | Killion et al. |
| 5,903,868 A | 5/1999 | Yuen et al. |
| 6,021,207 A | 2/2000 | Puthuff et al. |
| 6,021,325 A | 2/2000 | Hall |
| 6,163,338 A | 12/2000 | Johnson et al. |
| 6,163,508 A | 12/2000 | Kim et al. |
| 6,226,389 B1 | 5/2001 | Lemelson et al. |
| 6,298,323 B1 | 10/2001 | Kaemmerer |
| 6,359,993 B2 | 3/2002 | Brimhall |
| 6,400,652 B1 | 6/2002 | Goldberg et al. |
| 6,415,034 B1 | 7/2002 | Hietanen |
| 6,567,524 B1 | 5/2003 | Svean et al. |
| RE38,351 E | 12/2003 | Iseberg et al. |
| 6,661,901 B1 | 12/2003 | Svean et al. |
| 6,728,385 B2 | 4/2004 | Kvaloy et al. |
| 6,748,238 B1 | 6/2004 | Lau |
| 6,754,359 B1 | 6/2004 | Svean et al. |
| 6,804,638 B2 | 10/2004 | Fiedler |
| 6,804,643 B1 | 10/2004 | Kiss |
| 7,072,482 B2 | 7/2006 | Van Doorn et al. |
| 7,107,109 B1 | 9/2006 | Nathan et al. |
| 7,209,569 B2 | 4/2007 | Boesen |
| 7,430,299 B2 | 9/2008 | Armstrong et al. |
| 7,433,714 B2 | 10/2008 | Howard et al. |
| 7,450,730 B2 | 11/2008 | Bertg et al. |
| 7,477,756 B2 | 1/2009 | Wickstrom et al. |
| 7,562,020 B2 | 7/2009 | Le et al. |
| 7,756,285 B2 | 7/2010 | Sjursen et al. |
| 7,778,434 B2 | 8/2010 | Juneau et al. |
| 7,920,557 B2 | 4/2011 | Moote |
| 8,014,553 B2 | 9/2011 | Radivojevic et al. |
| 8,493,204 B2 | 7/2013 | Wong et al. |
| 8,750,295 B2 | 6/2014 | Liron |
| 9,037,458 B2 | 5/2015 | Park et al. |
| 9,123,343 B2 | 9/2015 | Kurki-Suonio |
| 9,135,797 B2 | 9/2015 | Couper et al. |
| 2001/0003542 A1 | 6/2001 | Kita |
| 2001/0046304 A1 | 11/2001 | Rast |
| 2002/0083025 A1 | 6/2002 | Robarts |
| 2002/0106091 A1 | 8/2002 | Furst et al. |
| 2002/0118798 A1 | 8/2002 | Langhart et al. |
| 2003/0016129 A1 | 1/2003 | Menard |
| 2003/0083011 A1 | 5/2003 | Hailer |
| 2003/0144829 A1* | 7/2003 | Geatz ................... G16H 10/60 703/22 |
| 2003/0151982 A1 | 8/2003 | Brewer |
| 2003/0161097 A1 | 8/2003 | Le et al. |
| 2003/0165246 A1 | 9/2003 | Kvaloy et al. |
| 2003/0169234 A1 | 9/2003 | Kempisty |
| 2003/0193426 A1 | 10/2003 | Vidal |
| 2004/0042103 A1 | 3/2004 | Mayer |
| 2004/0070491 A1 | 4/2004 | Huang |
| 2004/0109668 A1 | 6/2004 | Stuckman |
| 2004/0125965 A1 | 7/2004 | Alberth, Jr. et al. |
| 2004/0190737 A1 | 9/2004 | Kuhnel et al. |
| 2004/0196992 A1 | 10/2004 | Ryan |
| 2004/0203351 A1 | 10/2004 | Shearer |
| 2005/0060232 A1 | 3/2005 | Maggio |
| 2005/0078838 A1 | 4/2005 | Simon |
| 2005/0123135 A1 | 6/2005 | Hunt |
| 2005/0123146 A1 | 6/2005 | Voix et al. |
| 2005/0159275 A1 | 7/2005 | Bullman |
| 2005/0288057 A1 | 12/2005 | Lai et al. |
| 2006/0067551 A1 | 3/2006 | Cartwright et al. |
| 2006/0083395 A1 | 4/2006 | Allen et al. |
| 2006/0092043 A1 | 5/2006 | Lagassey |
| 2006/0154642 A1* | 7/2006 | Scannell, Jr. .......... G08B 7/066 455/404.1 |
| 2006/0195322 A1 | 8/2006 | Broussard et al. |
| 2006/0204014 A1 | 9/2006 | Iseberg et al. |
| 2006/0282021 A1* | 12/2006 | DeVaul ................. A61B 5/0205 600/595 |
| 2007/0021073 A1 | 1/2007 | Gratton |
| 2007/0043563 A1 | 2/2007 | Comerford et al. |
| 2007/0060446 A1 | 3/2007 | Asukai |
| 2007/0071264 A1 | 3/2007 | Baechler |
| 2007/0077784 A1 | 4/2007 | Kalayjian |
| 2007/0086600 A1 | 4/2007 | Boesen |
| 2007/0189544 A1 | 8/2007 | Rosenberg |
| 2007/0206829 A1 | 9/2007 | Weinans et al. |
| 2007/0268119 A1 | 11/2007 | Cram |
| 2007/0291953 A1 | 12/2007 | Ngia et al. |
| 2008/0037801 A1 | 2/2008 | Alves et al. |
| 2008/0146890 A1* | 6/2008 | LeBoeuf ............... A61B 5/4839 600/300 |
| 2008/0159547 A1 | 7/2008 | Schuler |
| 2008/0165988 A1 | 7/2008 | Terlizzi et al. |
| 2009/0010456 A1 | 1/2009 | Goldstein et al. |
| 2009/0016540 A1 | 1/2009 | Heningsen Nielsen et al. |
| 2009/0024234 A1 | 1/2009 | Archibald |
| 2010/0061564 A1 | 3/2010 | Clemow et al. |
| 2010/0119077 A1 | 5/2010 | Platz |
| 2010/0274100 A1* | 10/2010 | Behar ................... G16H 40/67 600/301 |
| 2010/0296668 A1 | 11/2010 | Lee et al. |
| 2011/0096939 A1 | 4/2011 | Ichimura |
| 2011/0264447 A1 | 10/2011 | Visser et al. |
| 2011/0293103 A1 | 12/2011 | Park et al. |
| 2014/0062678 A1 | 3/2014 | de Clercq |
| 2016/0104452 A1 | 4/2016 | Guan et al. |

OTHER PUBLICATIONS

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

(56) References Cited

OTHER PUBLICATIONS

Mauro Dentino, John M. McCool, and Bernard Widrow, Adaptive Filtering in the Frequency Domain, Proceedings of the IEEE, vol. 66, No. 12, Dec. 1978.

* cited by examiner

DESIGNER CONTROL DEVICES

CROSS-REFERENCE TO RELATED APPLICATIONS

This application is a continuation of and claims priority to U.S. application Ser. No. 14/335,902, filed on 19 Jul. 2014, which is an continuation of U.S. application Ser. No. 12/111,005 filed on 28 Apr. 2008 and further claims the benefit of U.S. provisional patent application No. 60/914,319 filed on 27 Apr. 2007, the disclosures of which are incorporated herein by reference in their entirety.

FIELD

The present invention relates to designer control devices, and in particular, though not exclusively, to a wearing customizable remote control device.

BACKGROUND

Several methods and devices have been developed to monitor the biometrics of a wearer. Additionally, several devices exist to remotely control some electronic devices (e.g., a TV remote). No device currently on the market exists that is externally wearer customizable and configured to control an audio device.

SUMMARY

At least one exemplary embodiment is directed to a wearable remote control assembly configured to control media devices and which may promote brand loyalty, longevity and continuity of a marketing message, such as a hearing-safety awareness campaign or music artist. The remote control device may be worn as a finger ring, badge, broche, or as a bracelet, and may have an appearance customized by the user with a web-based program, and the appearance may be dynamically changed using a programmable LED, LCD or plasma display. The remote control device may contain transducers such as microphones, loudspeakers, which may be detachable, as well as biometric sensing systems to monitor user health such as user heart rate, blood pressure or blood oxygen content. In some exemplary embodiments, audio signal processing may be undertaken on the remote control device with a microprocessor. Computer memory housed in the remote control assembly may also store biometric data such as personal or security clearance information or data for financial transactions such as for wireless purchasing, and audio data may also be stored in RAM computer memory on the remote control device.

At least one exemplary embodiment of the present invention provides for a functional marketing tool that serves as a remote control device to operate different media devices such as a headset for sound reproduction or recording. In some embodiments, the remote control can receive data from biometric sensors such as heart-rate monitors, and can transmit control data to audio devices such as Portable Media Players (PMPs) and audio headsets.

At least one exemplary embodiment of the remote control system is for a design comprising no user display and a small number of control buttons. The remote control device in this particular embodiment is intended to be worn as a finger ring or bracelet, though could be worn as a pendant from a necklace, around the user's ankles or upper arm. A marketing logo may be located on the device, such as an engraving on a bracelet advertising a particular brand, person, icon or campaign such as a hearing damage awareness campaign.

In at least one exemplary embodiment, the remote control device operates not just level control of reproduced audio content (e.g. music audio from a PMP or voice audio from a telecommunications network), but also recording operations using one or more microphone signals in the headset device. If these microphones are located substantially near the entrance to the user's occluded or partly occluded ear canal, then a binaural recording can be made. Sound recordings can also be made using microphones housed within the remote control assembly, or connected to the remote control assembly using a wired or wireless data communication system.

At least one exemplary embodiment is directed to a remote control device that can display a sound exposure profile that takes into account the sound exposure at the user's eardrum over a recent history (e.g. the last day). The sound pressure level (SPL) may be measured empirically using microphones in the user's occluded ear canal, or externally with microphones at or near to the entrance to the user's ear canal. The remote control device can display the "SPL Dose" as a numerical value corresponding to the accumulated dose as a percentage before temporary or permanent threshold shift may occur, or it can display a remaining time value, which informs the user how long (e.g. in minutes) the user has until temporary or permanent threshold shift may occur based on current ambient sound levels and levels of reproduced audio content.

In at least one exemplary embodiment the appearance of the remote control may be modified dynamically by the user (customization) or automatically depending on the operating mode to display different control interface screens or user-defined text and/or logos or text and/or logos for marketing purposes. This is accomplished by changing the display of the touch-screen, or changing the display behind fixed buttons, or changing the colors of the components used to create the remote control assembly. The appearance may change dynamically in response to a locally transmitted data signal, e.g. to inform the user of a nearby product vending machine or particular location or event which may be of interest to the user (e.g. a special offer on a product or a nearby museum).

In at least one exemplary embodiment the remote control assembly includes a low battery warning system to inform the user of the remaining battery status of the remote control device, and the remaining battery status of other audio devices that the remote control device communicates with, such as audio headsets, PMPs, mobile phone. Depending on user specifications, the system either: presents a series of audio warning signals; updates a visual display with information and a warning message; automatically attenuates (attenuation) audio output using the DSP; stops audio playback entirely; generates a tactile warning (vibration, pressure, etc); or any combination of the methods described.

In at least one exemplary embodiment the remote control may be worn as a wrist-strap bracelet or necklace. In these embodiments, a provision is made for a biometric sensor, such as a heart-rate sensor. This may function by detecting micro-electronic modulations between sensors on either side of the remote control caused by electro-cardiac signals. In the exemplary embodiment, the user is provided with a visual display of the current heart-rate, and a corresponding auditory display. Depending on the operating mode, this auditory display may be as a simple beep synchronized with the heart-beat, or it may be in the form of a spatialized audio scene. For instance, if the user's ideal BPM is higher than the present BPM, then a spatial sound image (e.g. a beep or reproduced music) could be spatialized using HRTF processing to seem in front of the user. Furthermore, the current invention allows for transmission of the user's current blood-related health (e.g. heart rate) to be logged and/or transmitted to a second party, such as an emergency worker or military HQ to inform the remote party of the health of the user.

In at least one exemplary embodiment there exists a loudspeaker for monitoring audio signals transmitted from different audio devices which are controlled, such as mobile-phones or PMPs. This allows the user or other individuals to monitor such audio content without necessarily wearing a headset. Loudspeaker driving circuitry is housed within the remote control assembly, consisting of a digital-to-analog converter and analog amplification and frequency equalization circuitry to compensate for the sensitivity of the loudspeaker driver. In some embodiments, the loudspeaker assembly is detachable using a wired connection or self-powered wireless assembly.

Yet another exemplary embodiment includes a microphone for monitoring the local ambient sound field of the remote control device, and for transmitting the resulting microphone audio signal to different audio devices such as mobile-phones or PMPs. This facilitates the user or other individuals to speak directly into a microphone that may be mounted on the wrist-worn remote control device, which is especially useful in high-noise environments to bring the microphone closer to the individual's mouth. The microphone receiving circuitry is housed within the remote control assembly, consisting of a digital-to-analog converter and analog amplification and frequency equalization circuitry to compensate for the sensitivity of the microphone. In some embodiments, the microphone assembly is detachable using a wired connection or a wireless self-powered assembly.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS

Figure 1:
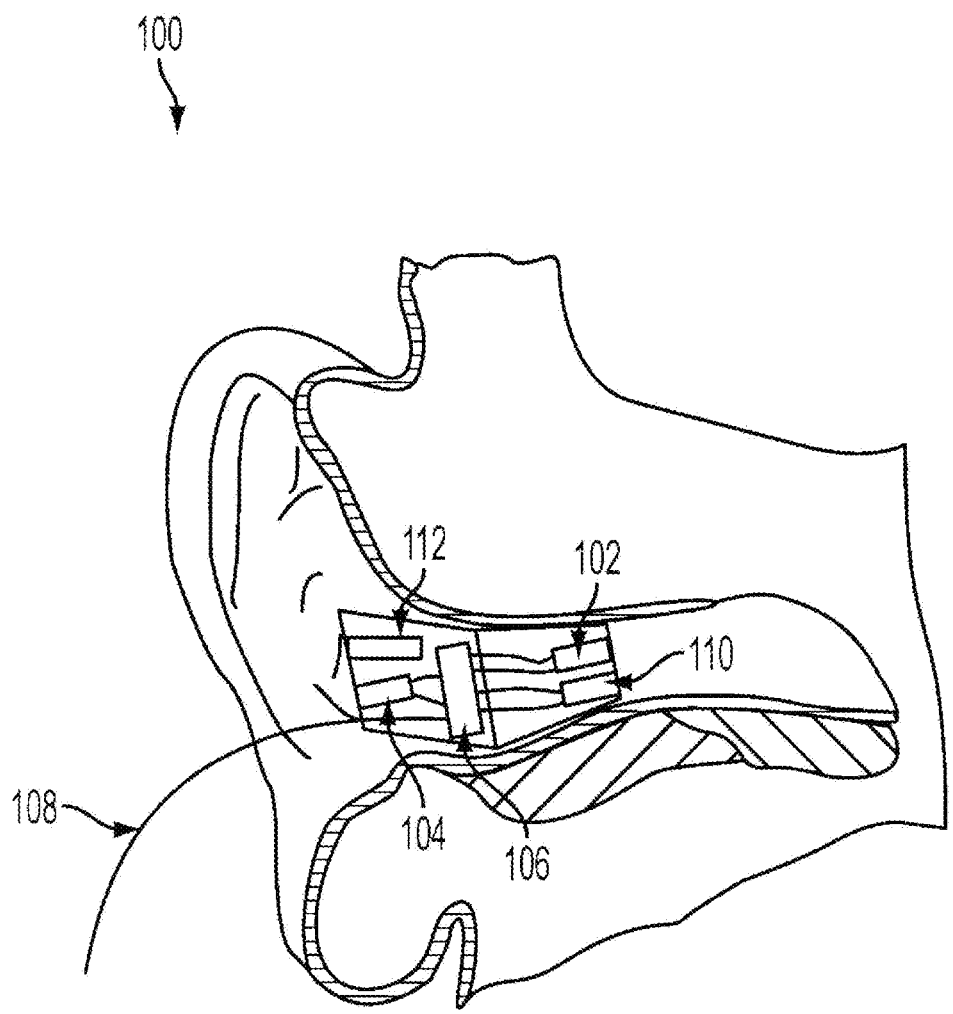
FIG. 1 is an illustration of an earpiece in an ear.

The following description of exemplary embodiment(s) is merely illustrative in nature and is in no way intended to limit the invention, its application, or uses.

Exemplary embodiments are directed to or can be operatively used to control various wired or wireless earpieces devices (e.g., earbuds, headphones, ear terminal, behind the ear devices or other acoustic devices as known by one of ordinary skill, and equivalents). Note that other non-earpiece devices can also be controlled and the invention is not limited by controlling an earpiece.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally exemplary embodiments are not limited to earpieces, for example some functionality can be implemented on other systems with speakers and/or microphones for example computer systems, PDAs, BlackBerry® smart-phones, cell and mobile phones, and any other device that emits or measures acoustic energy. Additionally, exemplary embodiments can be used with digital and non-digital acoustic systems. Additionally various receivers and microphones can be used, for example MEMs transducers, diaphragm transducers, for example Knowles' FG and EG series transducers.

Notice that similar reference numerals and letters refer to similar items in the following figures, and thus once an item is defined in one figure, it may not be discussed or further defined in the following figures.

Encouraging usage of a high-visibility marketing tool for consumers is enhanced by providing an incentive for the user. The present invention discloses a marketing device in the form of a user-wearable badge or item of jewelry that promotes wearability based upon the device serving functional control of at least one audio device. Additionally, the invention provides for bi-directional in-situ processing of audio signals, and provides the ability to record the user's ambient sound field using one or more microphones housed within the remote control device, or to monitor audio content user a loudspeaker that is housed in the remote control device.

In at least one exemplary embodiment of the present invention disclosed herein can undertake audio signal processing from a first portable media device such as a PMP, and transmits the processed audio to a second device, such as a headset.

In at least one exemplary embodiment of the present invention, this audio signal processing can be bi-directional, i.e. simultaneously processing audio from a first audio device to a second whilst processing audio from the second device and then transmitting this processed signal to the first device. The present invention furthermore an be designed as a marketing tool whereby the remote control unit undertaking the signal processing and controlling the portable media player devices is used to display a product logo or other insignia.

At least one exemplary embodiment of the present invention is designed to promote enhanced visibility for a marketing campaign, while it can control media devices, and is further designed to affect functionality of audio devices such as audio reproduction and recording with a user-worn headset.

At least one exemplary embodiment of the present invention allows for activation of recording and subsequent playback of a user's local ambient sound field using microphones mounted near or at the entrance to the user's occluded eardrum (in other words; a binaural recording) or microphones housed within the remote control device itself.

At least one exemplary embodiment of the present invention may simultaneously operate a plurality of devices, and at least one exemplary embodiment of the present invention can be designed to operate at least one headset for purposes such as audio recording, monitoring and reproduction, using loudspeakers and microphones embedded in the headset and/or loudspeakers and microphones embedded in the remote control device.

Furthermore, at least one exemplary embodiment the present invention can be designed to be worn by the user as jewelry, such as in the form of a wrist strap or necklace. Also, the remote control device in the present invention allows for user customization, such as different colors, different clasp mechanisms (such as fabric or metallic straps) using a web-based customization process.

At least one exemplary embodiment of the present invention provides for heart-rate information (e.g. beats-per-minute) to be transmitted to the user-worn headset system and to (optionally) auralize the auditory display using personalized or non-personalized head-related transfer function (HRTF) processing. This could give the effect of spatializing a target or optimum heart-rate feature (e.g. BPM or blood pressure) so as to act as an incentive for the user. For instance, if the user's ideal BPM is higher than the present BPM, then a spatial sound image (e.g. a beep or reproduced music) could be spatialized using HRTF processing to seem in front of the user. Furthermore, at least one exemplary embodiment of the current invention allows for transmission of the user's current blood-related health (e.g. heart rate) to be logged and/or transmitted to a second party, such as an emergency worker or military HQ to inform the remote party of the health of the user.

At least one exemplary embodiment is directed to a headset which can be used with the present invention as is illustrated in FIG. 1. The embodiment is a small headphone that is inserted in the ear of the user. The headphone can include the sound-attenuating earplug 100 inserted into the ear canal. At the inner (eardrum-facing) surface of the plug, an ear-canal loudspeaker receiver (ECR) 102 is located for delivering the audio signal to the listener. At the outer (environment-facing) surface of the plug, an ambient-sound microphone (ASM) 104 is located. Both the loudspeaker 102 and the microphone 104 are connected to the electronic signal processing unit 106. The signal processing unit 106 also has a connector 108 for input of the audio signal. This connector medium 108 may be a wireless signal such as a conventional radio or Bluetooth protocol. Additionally, an ear-canal microphone (ECM) 110 is placed at the inner (eardrum-facing) surface of the plug and an external loudspeaker 112 is placed on the outer (environment-facing) surface of the plug for performing other functions of the headphone system not described here (such as monitoring of sound exposure and ear health conditions, headphone equalization, headphone fit testing, noise reduction, and customization).

Figure 2:
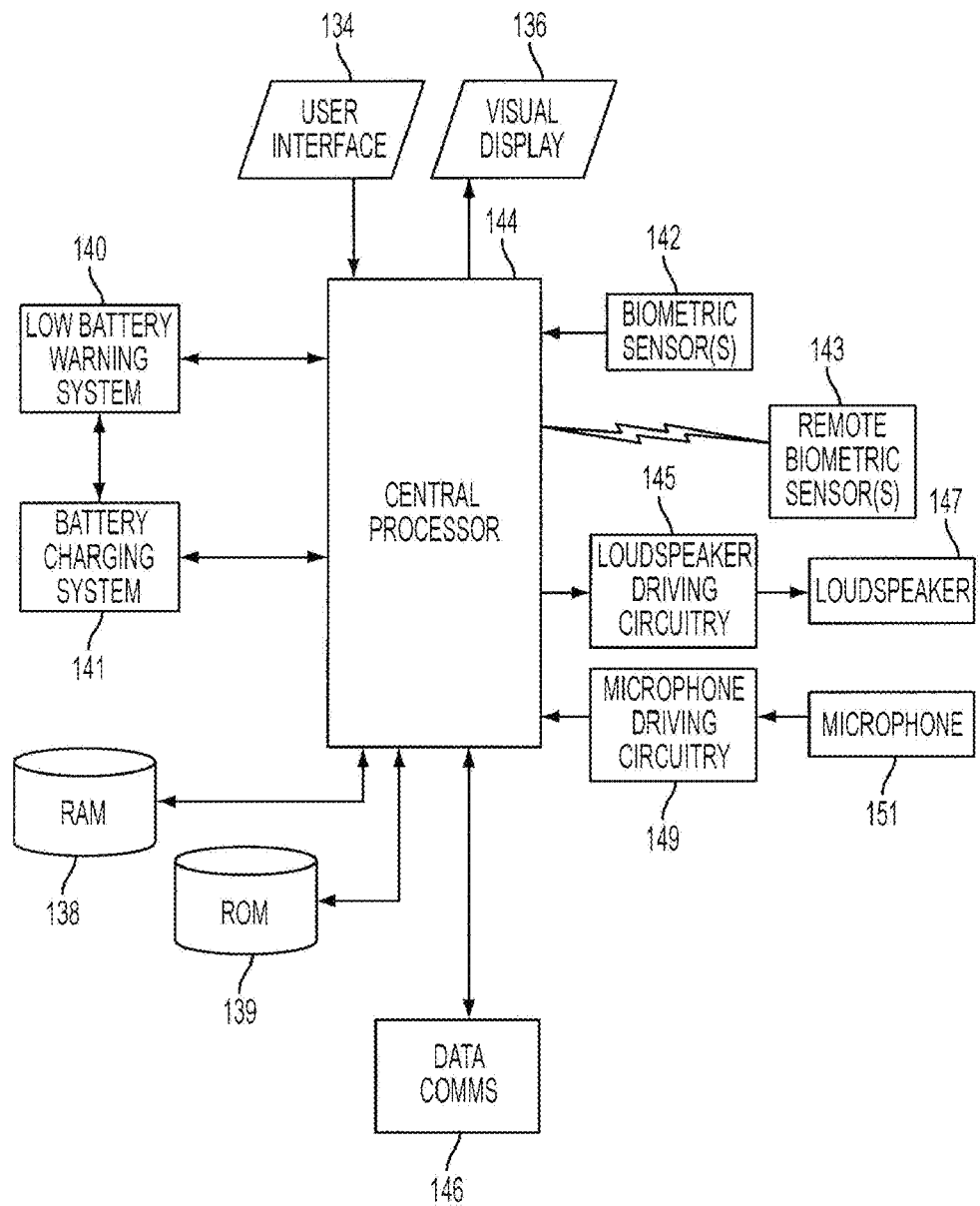
FIG. 2 is a block diagram of a system in accordance with at least one exemplary embodiment.

FIG. 2 gives an overview of the User Wearable Remote Control device showing components that may be present or absent depending on the particular embodiment. The remote control device can include, as its principle components, a user interface 134, which may include a miniature keyboard, one or more scroll wheels, push buttons, or (in the exemplary embodiment) a touch-sensitive screen that can also be used as a visual display 136, or a combination of the above. The central processing unit 144 is a general purpose processor and in some embodiments is combined with an Application-Specific Integrated Circuit (ASIC) (not shown), or in some other combination involving a general purpose processor and an ASIC combined in one unit (such as an FPGA). The processor 144 undertakes control of the transmission of audio input and output signals to and from the computer memory RAM unit 138, signal processing for the low battery warning system 140, control and processing of data from the local (wired) biometric sensor (e.g. heart-rate detector) 142 or remote, second biometric sensor 143, and control of the audio and control data communication assembly 146. The processor 144 detects the presence of a power (battery) charging device such as an inductance or wired charging unit, and may initiate charging of the built-in battery with system 141. Computer memory in RAM form 138 for containing user data or audio, and computer memory in ROM form 139 for storing program code, are housed in the remote control device assembly.

In some embodiments there exists a loudspeaker 147 for monitoring audio signals transmitted from different audio devices which are controlled, such as mobile-phones or PMPs. This allows the user or other individuals to monitor such audio content without necessarily wearing a headset. Loudspeaker driving circuitry 145 is housed within the remote control assembly, consisting of a digital-to-analog converter and analog amplification and frequency equalization circuitry to compensate for the sensitivity of the loudspeaker driver. In some embodiments, the loudspeaker assembly is detachable using a wired connection or self-powered wireless assembly.

Another embodiment includes a microphone 151 for monitoring the local ambient sound field of the remote control device, and for transmitting the resulting microphone audio signal to different audio devices such as mobile-phones or PMPs. This allows the user or other individuals to speak directly into a microphone that may be mounted on the wrist-worn remote control device, which is especially useful in high-noise environments to bring the microphone closer to the individual's mouth. The microphone receiving circuitry 149 is housed within the remote control assembly, consisting of a digital-to-analog converter and analog amplification and frequency equalization circuitry to compensate for the sensitivity of the microphone. In some embodiments, the microphone assembly is detachable using a wired connection or wireless self-powered assembly.

The data communications assembly 146 undertakes control of audio and non-audio (control) data between the central processor and other audio devices such as a PMP 148 (FIG. 3B) and one or more headsets such as that described in FIG. 1. The audio data may be relayed directly from one device to the other, or may be processed first by the central processor 144. The communication assembly 146 may consist of either or both wired and wireless communication devices; such as radio transceivers for Bluetooth or conventional radio audio and non-audio data transmission and associated signal processing assemblies (such as ADC and DACs, signal amplifiers etc. familiar to those skilled in the art), or assemblies for directly transceiving analog audio signals such as with one or more conventional stereo ⅛" input jacks or optical SPD IF input jacks.

Figure 3A:
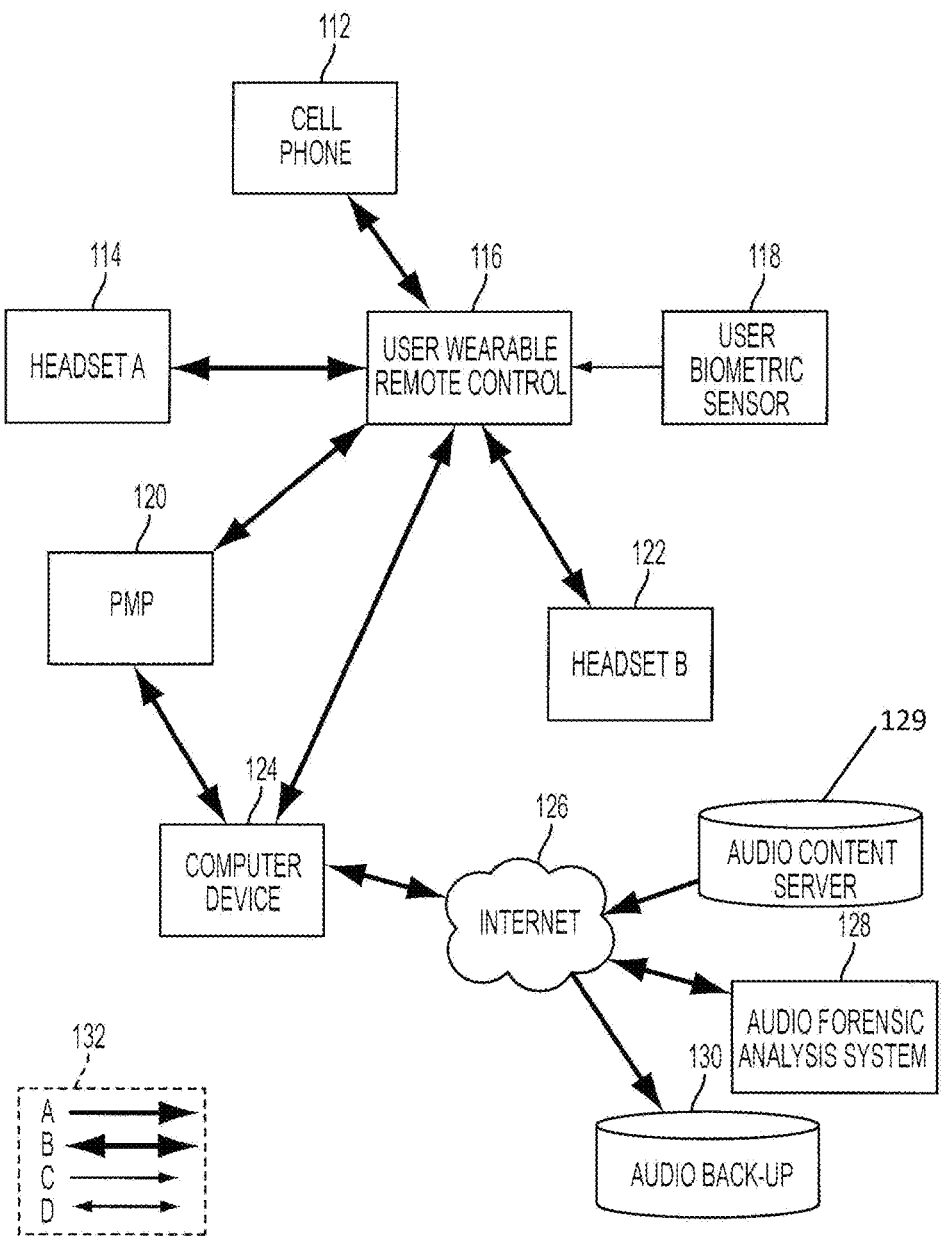
FIG. 3A is a block diagram of a system connected to an internet in accordance with at least one exemplary embodiment.

FIG. 3A gives an overview of the User Wearable Remote Control device 116 in relation to various audio technology devices and systems it is intended to be used with. The connections to these devices and systems are shown as bi-directional or single-ended arrows. As shown in box legend 132, these arrows may be double-walled (A, B) or single walled (C, D). The notation used through the drawings is that mixed audio and control signals are represented with double-walled arrows, and control-only signals with single walled. Control signals mean any signal that does not directly represent audio signals. The direction of the arrow indicates the direction of audio or control signal flow from one unit to the other, as familiar to those skilled in the art. Typical audio devices the remote control device is used with in its exemplary embodiment are: cell phones 112, headset systems 114 and 122 such as that described in FIG. 1 (but conventional headphone systems could also be used); user biometric sensors 118; Portable Media Players 120 such as hard-drive or RAM-chip mp3 players, digital radio players, portable DVD players or portable electronic gaming units; and computer devices 124 such as laptops, PDAs, or desktop computers. The audio devices in the previous list may be used simultaneously with remote control device 116 and at least one headset 114, or in any combination thereof. The computer devices 124 may be connected to the internet 126 allowing the user to upload audio content (from audio content server 129) to a PMP device 120 via the remote control device 116 or directly from the computer device 124 to the PMP 120. Audio content may also be downloaded via computer device 124, the internet 126 to a back-up audio data server 130. Such audio content may be from recordings made with ASM signals (from ASM 104 (FIG. 1)), microphones 151 (FIG. 2) housed in the remote control assembly or Ear Canal Microphone signals (from ECM 110 (FIG. 1)) with one or more headsets 114, 122. These recorded audio signals may also be analyzed by an audio forensic analysis system 128 for purposes such as speech-to-text analysis, or accident determination. Data analysis by forensic system 128 may be presented to the user via a visual or auditory display with the remote control device 116. The optional loudspeaker 147 and microphone 151 housed shown in FIG. 2 are not shown in this figure.

Figure 3B:
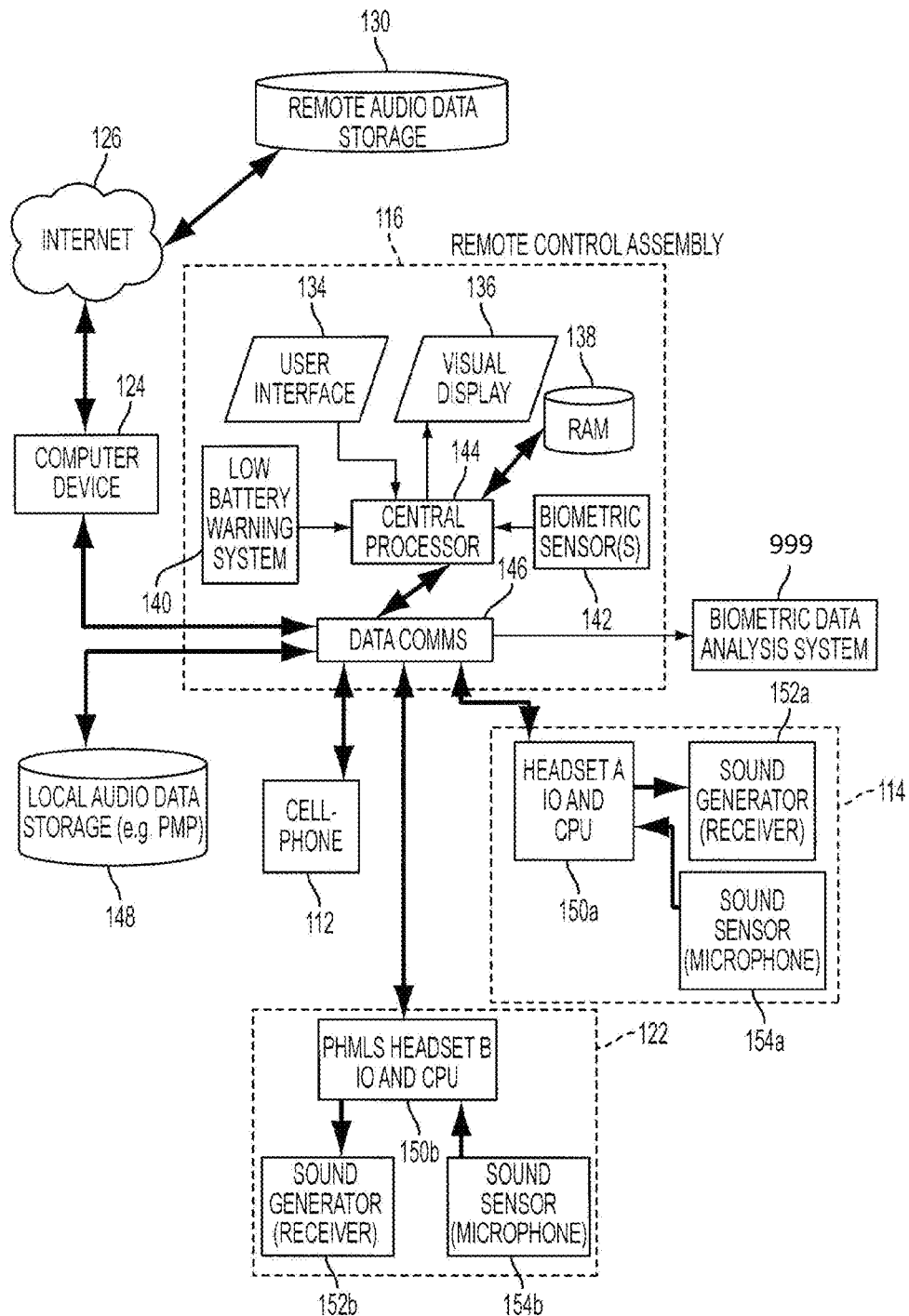
FIG. 3B is a block diagram of a system that can control several devices in accordance with at least one exemplary embodiment.

FIG. 3B gives a more detailed overview of user wearable remote control device and some particular audio devices described in the embodiment presented in FIG. 3A, as well as biometric data analysis system 999. The central processing unit 144 may undertake audio signal processing on input signals from a number of devices, such as a cell-phone 112 and/or PMP 148 (e.g. mp3 player, portable DVD player). FIG. 3B also illustrates that headsets 114, 122 may include respective input/output (IO) and CPU 150, sound generator (receiver) 152 and sound sensor (microphone) 154.

Figure 4A:
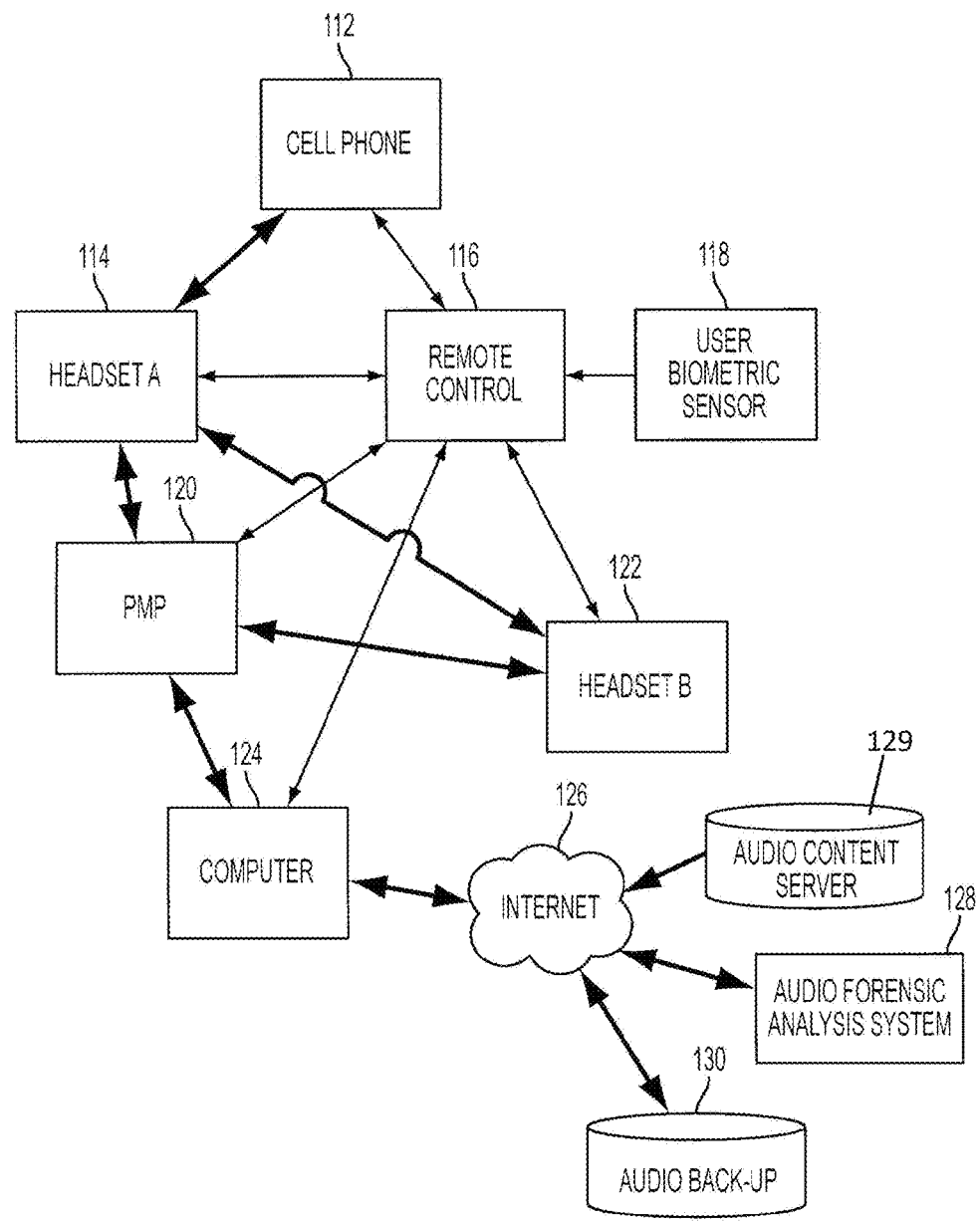
FIG. 4A is a block diagram of a system that can control several devices with access to an internet.
Figure 4B:
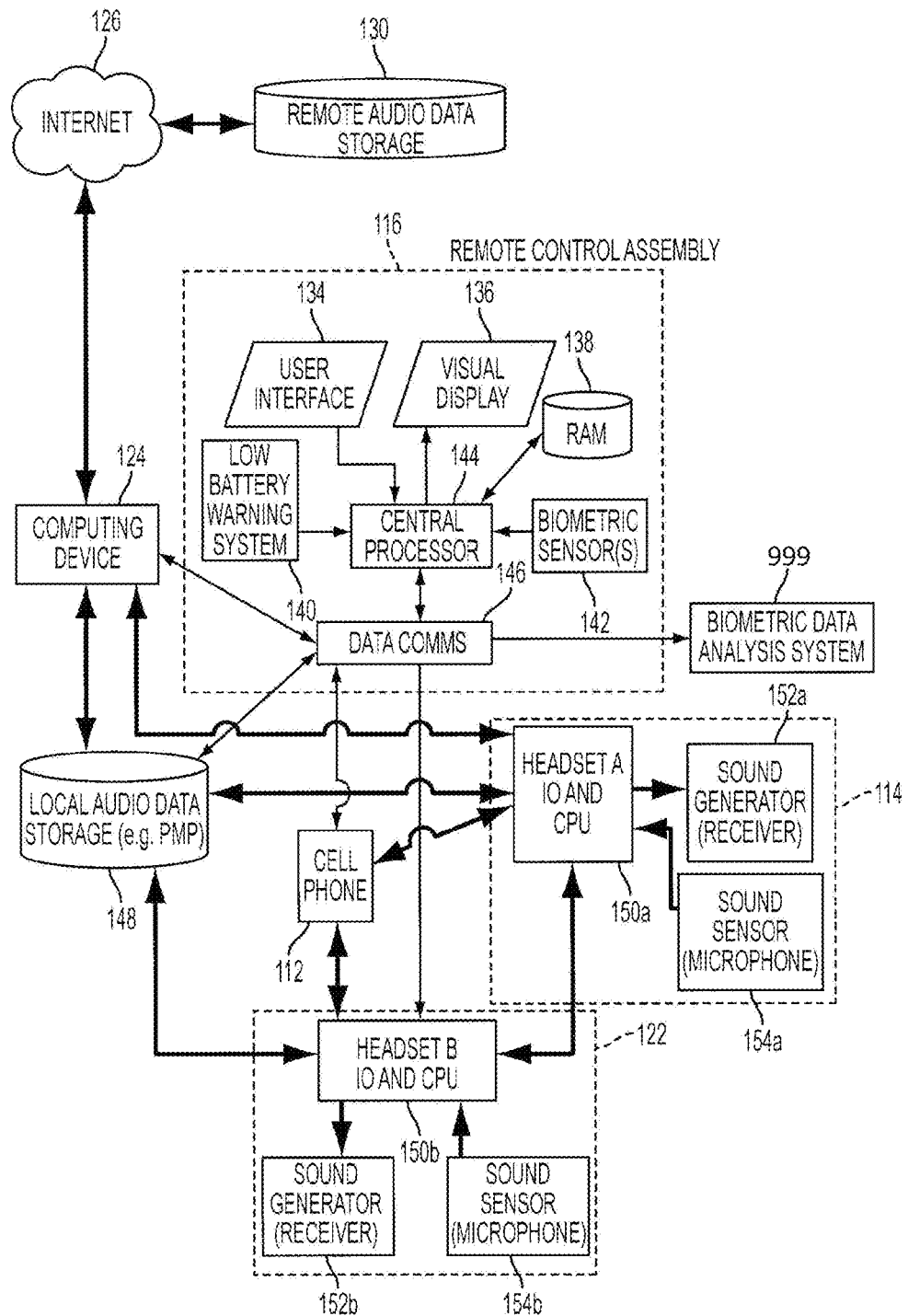
FIG. 4B is a block diagram of a system that can control several devices with access to an internet and can access remote audio data storage.

FIGS. 4A and 4B show another embodiment of the remote control device shown in FIGS. 3A and 3B. The difference between the two embodiments is that in FIGS. 4A and 4B there is no transmission of audio signals through the remote control device itself; in this embodiment the audio signals are transmitted directly between audio devices such as a PMP 120 and headset 114.

Figure 5:
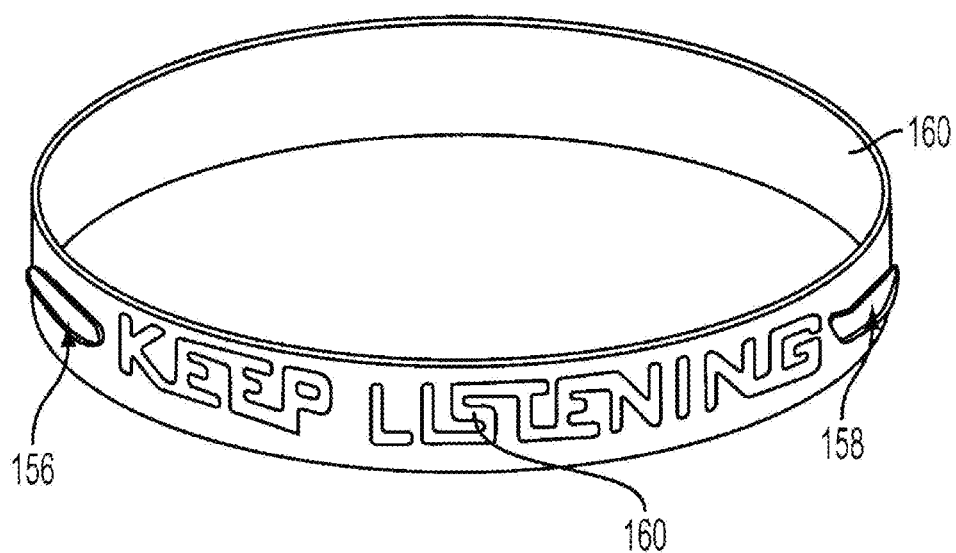
FIG. 5 illustrates an example of a wearer piece of jewelry in accordance with at least one exemplary embodiment.

FIG. 5 shows example artwork of the current invention in a particular embodiment as a tool for increasing awareness of a non-commercial listening awareness campaign. In the particular example, the logo "keep listening" 160 is engraved on the remote control device bracelet 161, and shows that the user endorses this campaign and advertises the campaign with a fashionably pleasing aesthetic. The controls for the device in this particular embodiment consist of two simple buttons 156, 158 which may be used to control volume level, power (e.g. by pressing the two buttons together), or controlling the currently auditioned song track (e.g. advancing track by holding down button 158). Signal processing and battery power may be contained within the body of the bracelet 161, and the control data transmission circuitry may use a wireless system with the wireless aerial embedded in the user-worn remote control.

Figure 6:
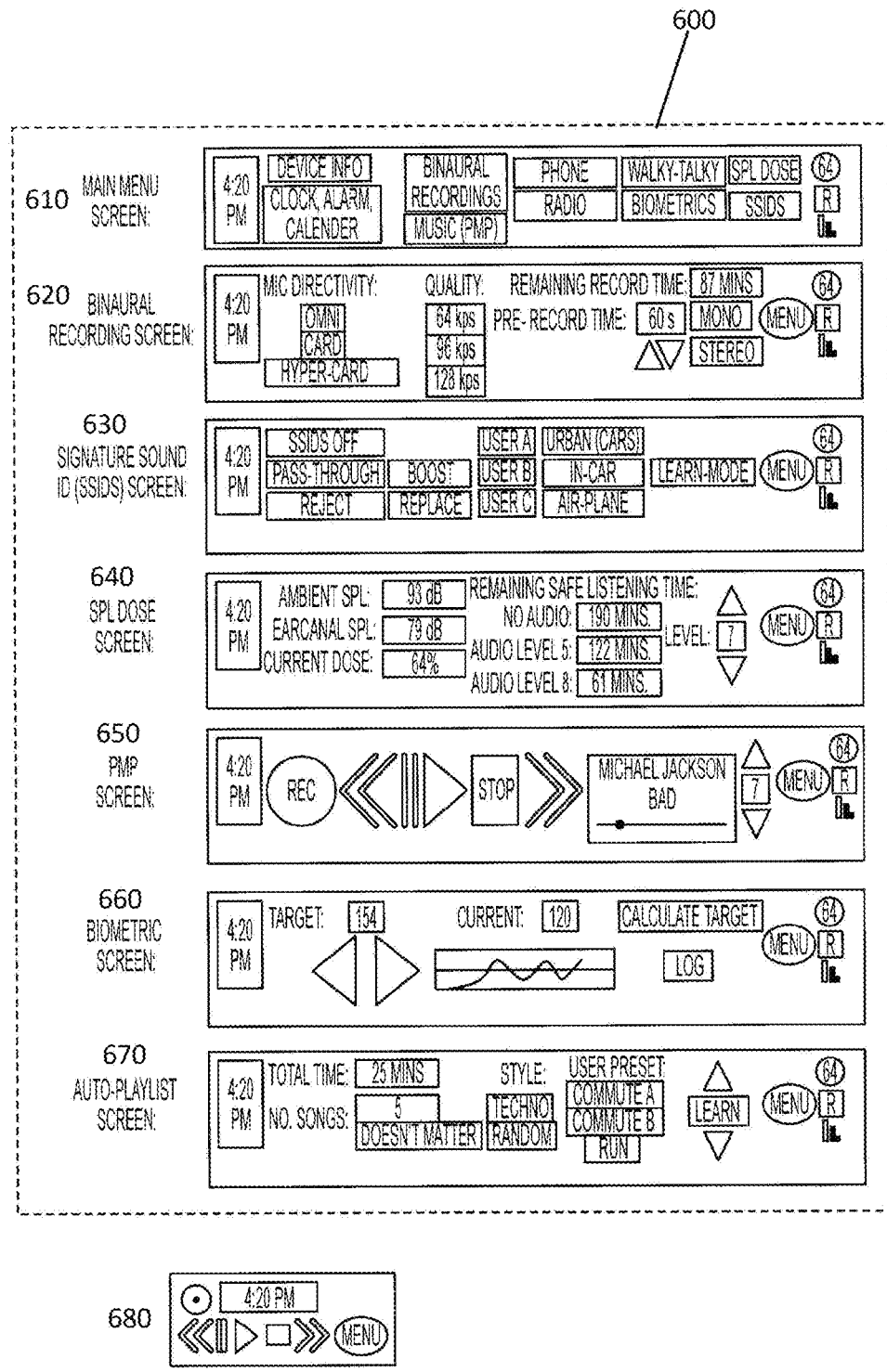
FIG. 6 illustrates a Graphic User Interface (GUI) in accordance with at least one exemplary embodiment.

FIG. 6 gives an overview of a combined user-interface display 600 and response screen (e.g., 610, 620, 630, 640, 650, 660, 670), as might be worn on a wrist band (the screen (e.g., 610, 620, 630, 640, 650, 660, 670) may wrap around with a flexible or articulated joint), or as a necklace pendant. Alternatively, a smaller screen may be used as shown in the lowest FIG. 680). In some embodiments, the screen may be non touch sensitive, and scrolling wheels and buttons used to select different operating modes and system control parameters.

ADDITIONAL EXEMPLARY EMBODIMENTS

Exemplary Embodiment Example 1

1. At least one exemplary embodiment of the remote control system for controlling reproduction of audio from a first media device (such as a PMP) with a second sound reproduction device (such as a headset). The remote control device can be worn anywhere on the user's body or attached to the user's clothes. For instance, the remote control could be worn as a finger ring, arm or leg bracelet, a pendant for a necklace, or on a waist-belt. A marketing logo can be incorporated in the device, such as an engraving on a bracelet advertising a particular brand or public awareness campaign. Audio signal processing from the first media device may be undertaken on the remote control device with an embedded ASIC, and this processed signal transmitted to a second audio reproduction and/or recording device whilst simultaneously processing signals from the second device before transmission to the first device. This user-worn functional jewelry can include:
   A. An attaching device such as a metallic or plastic ring which may be flexible or contain elastic components to fix the remote control device to the user's arm, leg or finger, or contain a clasp to fix to a necklace or waist-belt.
   B. A user interface for controlling media devices such as Portable Media Players (PMPs) to affect control of these media devices, such as level of Audio Content, navigation of audio playback and recording (for example; pause, stop, play, next track, previous track etc.).
   C. A user interface for affecting processing of audio signals from media devices such as PMPs for purposes such as frequency equalization, level control, adaptive noise control filtering.
   D. A user interface for controlling audio reproduction and/or sound recording devices such as at least one headset worn by either the user or by multiple people including the user.
   E. At least one application-specific integrated circuit (ASIC) or a general-purpose IC housed within the body of the user wearable remote control device to undertake either or both audio signal processing and Control Data processing such as decision logic and processing the user interface signals.

F. A Control Data communication system such as a wireless or wired data transmitter to transfer data.

G. An optional Audio Data transmission system for controlling audio playback on a first audio device, or between a plurality of audio devices such as a PMP and a headset.

H. A Control Data transmission system for functions such as playback, recording or activation of audio devices such as PMPs (see part C).

I. A battery power system that can be recharged using a wireless induction or wired system.

J. Non-volatile and/or volatile RAM type computer memory.

K. Non-volatile and/or volatile ROM type computer memory.

Exemplary Embodiment Example 2

2. Another exemplary embodiment includes the system of embodiment 1, wherein a user visual or auditory display exists to inform the user of the functional status of the remote control device and (in some embodiments) the functional status of other audio devices. This visual display provides the following functionality;

A. A user display to inform the user of the audio recording status of the user worn headset, such as the remaining record time, audio signal bit rate, number of audio channels, audio signal level and frequency content. This may be as a visual indicator on a user display and/or an auditory display system whereby speech or non-speech sounds are generated with increasing perceptual intrusion (e.g. increasing level) as the remaining computer memory or hard-disc level of one of these audio devices decreases.

B. A user display to inform the user of the audio playback status of the user worn headset, such as audio signal bit rate, number of audio channels, audio signal level and frequency content.

C. A visual display to inform other individuals (i.e. other than the user) that the remote control device user is listening to Audio Content (Audio Data, e.g. music or a voice audio signal) and may therefore not wish to be disturbed or may not be able to hear the other individuals. A different colored light may be used to represent different user listening states.

Exemplary Embodiment Example 3

3. Another exemplary embodiment includes the system of embodiment 1, wherein the at least one sound reproduction device of part (D) comprises:

A. An earplug that forms a seal in the ear canal of the user.

B. An earphone body that may be separate from the earplug that houses the electronic components of the earphone device.

C. One or more optional pressure equalization tubes to equalize the pressure on the ear-drum side of the earplug relative to the ambient pressure.

D. An assembly to monitor the acoustic field in a user's immediate environment using one or more Ambient Sound Microphones (ASMs) to monitor sound at the entrance to one or both occluded ear canals.

E. A signal processing circuit to amplify the signal from the ASM(s) and to equalize for the frequency sensitivity of the microphones.

F. An optional diaphragm to cover the ASM and provide the following exemplary capabilities:

Passive beam-forming using holes aligned in a predetermined direction. These holes may be filled with a material different from the material of the diaphragm. The directional sensitivity of the ASM may therefore by increased; e.g. in the direction of the user's mouth or perpendicular to the direction of the user's head so as to maximize the degree of electronic separation between ASM signals in opposite earphone devices (i.e. the left and right earphone of a pair worn by the same user).

Acoustically tuned sound absorbers to compensate for the frequency response of the ASM transducers. For instance, the diaphragm may be configured so as to transmit those frequencies that the ASM is less sensitive to with less attenuation.

Wind, headwear-abrasion, dust and debris shield to protect the ASM.

Use as a marketing tool for displaying a product brand or logo.

Use as a user interface, e.g. a button for activating a particular "sound pass-through" mode.

Use as a display to indicate operational status of the earphone device using front-lit or backlit illuminating means e.g. a multicolored LED.

Use as a diaphragm for creating sound to be monitored by other individuals near the earphone user, using a sound-creating object coupled to the diaphragm.

G. An assembly to monitor the acoustic field in an occluded ear canal consisting of a microphone mounted in an earplug that forms an acoustic seal of one or both ear canals of a user. (This is the Ear Canal Microphone; ECM.)

H. A signal processing circuit to amplify the signal from the ECM and to equalize for the frequency sensitivity of the ECM.

I. An optional signal processing circuit to amplify and process an Audio Content input signal (e.g. from a Personal Media Player, cell phone, or automatically-generated auditory warning signal).

J. A microprocessor assembly to undertake digital or analog signal processing on the ECM and ASM signals for the VOX.

K. A battery, low-battery warning, and battery charging assembly to power the electronic circuits in the earphone device.

L. A wired or wireless communications assembly to transmit audio and/or control signals to a remote control device.

M. A wired or wireless communications assembly to transmit audio signals and control data signals from the ECM and ASM signals from one earphone device to the other earphone device.

N. A wired or wireless communications assembly to transmit audio and/or control signals and control data signals from both earphone devices to an external system, such as a voice communication system or a second signal processing unit.

Exemplary Embodiment Example 4

4. Another exemplary embodiment of the present invention of embodiment 1 additionally comprises sound reproduction means, such as a loudspeaker, for monitoring audio signals transmitted from different audio devices that are controlled, such as mobile-phones or PMPs. This allows the user or other individuals to monitor such Audio Content without necessarily wearing a headset. Loudspeaker driving circuitry may be housed within the remote control assembly. In some exemplary embodiments, the loudspeaker assembly is detachable using a wired connection or wireless self-powered assembly.

Exemplary Embodiment Example 5

5. Another exemplary embodiment of the present invention of embodiment 1 additionally comprises a microphone for monitoring the local ambient sound field of the remote control device, and for transmitting the resulting microphone audio signal to different audio devices such as mobile-phones, computing devices or PMPs, or for storing the recorded microphone signal on RAM computer memory embedded within the remote control device. This allows the user or other individuals to speak directly into a microphone that may be mounted on the wrist-worn remote control device, which is especially useful in high-noise environments to bring the microphone closer to the individual's mouth. The microphone receiving circuitry is housed within the remote control assembly, consisting of a digital-to-analog converter and analog amplification and frequency equalization circuitry to compensate for the sensitivity of the microphone. In some exemplary embodiments, the microphone assembly is detachable using a wired connection or wireless self-powered assembly.

Exemplary Embodiment Example 6

6. Another exemplary embodiment includes the system of embodiment 1, wherein the system includes a low battery warning system to inform the user of the remaining battery status of the remote control device, and the remaining battery status of other audio devices which the remote control device communicates with, such as audio headsets, PMPs, mobile phone. Depending on user specifications, the system either:
  A. Presents a series of audio warning signals. These signals may be stored on computer memory or on a hard drive in the remote control device or on a separate media storage device such as a PMP. The signals may be speech, such as a verbal message indicating remaining battery time for a particular device, or may be non-speech, such as a bleep. The auditory warning sound may become increasingly intrusive as the battery of the particular device loses charge.
  B. Updates a visual display with information and a warning message;
  C. Automatically attenuates (attenuation) audio output using the DSP;
  D. Stops audio playback entirely;
  E. Generates a tactile warning (vibration, pressure, etc);
  F. Or any combination of the methods described above.

Exemplary Embodiment Example 7

7. Another exemplary embodiment for the present invention embodiment is contrary to the system of embodiment 1 in that audio signals are not communicated through the remote control device from a first audio device (e.g. PMP, mobile phone) to a second, but rather the audio signal is transmitted directly from the first device to the second, and the remote control affects audio reproduction by transmitting and receiver audio control signals (i.e. not Audio Data signals).

Exemplary Embodiment Example 8

8. Another exemplary embodiment for the present invention embodiment is a mix of the systems of embodiments 1 and 7 whereby some audio signals are communicated through the remote control device from one audio device (e.g. PMP, mobile phone) to the headset, but other audio signals may be communicated directly between audio devices.

Exemplary Embodiment Example 9

9. Another exemplary embodiment of the remote control device is for controlling the reproduction of audio from a Personal Media Player (PMP) and the recording of audio signals to the same PMP. Although only one PMP is used in this embodiment, a plurality of headsets may be used to reproduce the PMP audio from and to sample the personal sound field of the headset user(s).

Exemplary Embodiment Example 10

10. Another exemplary embodiment of the remote control device is for a permanent message to be visible on the device to increase visibility and show the user's support of a public service campaign such as hearing-loss awareness or another health-related campaign.

Exemplary Embodiment Example 11

11. Another exemplary embodiment of the remote control device is for a user-customizable style, whereby the colors of components comprising the wearable remote control can be customized using an online web-based program.

Exemplary Embodiment Example 12

12. Another exemplary embodiment of the remote control device is for a dynamically changing physical appearance, whereby a text message and/or audio message and/or logo may be displayed on a screen on the remote control device. The screen can be programmed and altered dynamically and may use a plasma screen display, LED or LCD display. The screen may be dynamically changed by sensing a signal transmitted from, for example, a vending machine, a retail store, or a museum.

Exemplary Embodiment Example 13

13. Another exemplary embodiment of the remote control device is for a detecting a transmitted radio signal from a "transmitting beacon" and informing the user with an auditory message transmitted from the remote control device to the headset. The signal may be transmitted from, for example, a vending machine, a retail store, or a museum, and the user may be informed using either a speech-message or non-speech message (e.g. music or a product signature "Ear-con"). The user may be informed of the location of the transmitting beacon using either a verbal message (e.g. informing the user of the street address with an auditory or visual display message), or with an auditory message which may be spatialized to help the user locate the transmitting beacon.

Exemplary Embodiment Example 14

14. Another exemplary embodiment of the remote control device provides for the monitoring and display of the device-user's heart rate using electro-cardiac sensors mounted on the device assembly or on a separate assembly. The display uses an auditory beacon whereby a beep-like pulse is sounded synchronously with the user's heartbeat. This particular embodiment can include:
  A. A biometric sensor to detect electro-cardiac signals on the users skin, such as with sensors mounted on either side of the wrist band housing the remote control device, or on a chest or upper-arm strap.
  B. A visual display to inform the user of their current cardiac status (e.g. heart rate or blood pressure).
  C. Alternative to or complimentary to the visual display, an auditory display may be used to inform the user of the heart rate. This could be with a verbal message informing the user of the heart rate at a time interval which may be user defined (e.g. every minute), or the heart rate may be related to a frequency pitch of a non-verbal message, e.g. a beep (short sine wave) with a pitch that increases with increasing pulse rate.
  D. A heart-rate logging system whereby the user's heart-rate profile is stored in computer memory in either the remote control device or on a separate assembly such as a PMP.
  E. A heart-rate data log communication system, whereby the heart rate profile may be transmitted using a wired or wireless data communication system directly to a computing device for analysis and for prognosis and advice to the user to seek medical consultation if any indication of cardiac health problems are detected.

Exemplary Embodiment Example 15

15. Another exemplary embodiment includes a spatial auditory display whereby signal filtering of an audio signal using, for instance, personalized or semi-personalized Head Related Transfer Functions (HRTF), may be undertaken to act as an auditory beacon indicating the user's current and target heart rate. In addition to the previous embodiment, this particular embodiment includes:
  A. An optional HRTF acquisition process whereby the user's personal or non-personal HRTF is acquired. There are many methods for acquiring personalized HRTFs disclosed in prior art such as using the reciprocity technique. Non-personalized HRTFs may be acquired by asking the user to select HRTF mixes of audio recordings according to particular sound characters, such as perceived separation of audio images or perceived naturalness or intelligibility (which may be measured with standard intelligibility tests known to those skilled in the art).
  B. Audio signal processing circuitry to filter audio signals (e.g. a speech message, music, or beep-pulse which is synchronized with the user's heart beat) so that the perceived sound image is located at an ego-centric distance related to the discrepancy between the user's actual and target heart rate. For instance, if the target and actual heart-rate are the same, the audio signal processing may be such that the image is located within the user's head. If the target is greater than the actual heart-rate, the audio signal processing may be such that the auditory image is located in front of the user's head. Such audio signal processing may include processing the Audio Content with HRTFs measured at different distances (i.e. ego-centric range) to the user's head. Other methods of controlling auditory image distance include affecting the ratio of artificial sound reflections (such as reverberation) to direct sound (i.e. the original Audio Content).

Exemplary Embodiment Example 16

16. A particular embodiment of the above systems includes an application-specific integrated circuit (ASIC) within the remote control assembly for undertaking DSP such as audio signal filtering for active noise control (familiar to those skilled in the art), equalization, voice recognition, and non-voice signal recognition on audio signals from, for instance, microphones on the user-worn headset, input Audio Content from a PMP or mobile-phone.

Exemplary Embodiment Example 17

17. Another exemplary embodiment of the present invention is for controlling video media players, such as portable DVD players, in addition to simultaneously controlling and processing audio signals.

Exemplary Embodiment Example 18

18. Another exemplary embodiment includes the system of embodiment 2, wherein a user visual or auditory display informs the user of a personal sound exposure history. The sound pressure level (SPL) may be measured using microphones in the user's occluded ear canal, or externally with microphones at or near to the entrance to the user's ear meatus, or in some embodiments using microphones housed in the remote control device. The remote control device may display the "SPL Dose" as a numerical value corresponding to the accumulated dose as a percentage before temporary or permanent threshold shift may occur, or it may display a remaining time value, which informs the user how long (e.g. in minutes) the user has until temporary or permanent threshold shift may occur based on current ambient sound levels and levels of reproduced Audio Content.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. For example, if words such as "orthogonal", "perpendicular" are used the intended meaning is "substantially orthogonal" and "substantially perpendicular" respectively. Additionally although specific numbers may be quoted in the claims, it is intended that a number close to the one stated is also within the intended scope, i.e. any stated number (e.g., 90 degrees) should be interpreted to be "about" the value of the stated number (e.g., about 90 degrees).

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

We claim:

1. A wearable device, comprising:
   a display;
   at least one processor;
   a biometric sensor configured to generate a biometric sensor data of a user while the user wears the wearable device; and
   a microphone,
   wherein, while the wearable device is worn by the user, the at least one processor performs operations comprising:
      receiving the biometric sensor data;
      capturing, using the microphone, an ambient sound of an environment, wherein the biometric sensor data is received and the ambient sound is captured while the wearable device is worn by the user;
      determining a sound pressure level (SPL) of the ambient sound;
      determining a SPL dose of a personal sound exposure of the user based on the SPL of the ambient sound, wherein the SPL dose comprises a percentage of an accumulated SPL dose or a time remaining value before a threshold shift occurs;
      wirelessly transmitting the biometric sensor data to an electronic device belonging to a second party; and
      outputting the SPL dose to the user,
   wherein the wearable device is at least one of an earphone, a headset having two earphones, a wrist-worn device, or a neck-worn device.

2. The wearable device of claim 1, wherein the biometric sensor comprises an electro-cardiac sensor.

3. The wearable device of claim 2, wherein the biometric sensor data includes a heart rate of the user, wherein the at least one processor plays back, through at least one speaker, sound based on the user's heart rate.

4. The wearable device of claim 3, wherein the sound comprises a verbal message informing the user of the user's heart rate that is played back at user-defined time intervals.

5. The wearable device of claim 3, wherein the at least one processor performs an operation that includes producing a heart-rate profile of the user based on the heart rate, wherein the heart-rate profile is wirelessly transmitted to the electronic device.

6. The wearable device of claim 1, wherein the display is a touch-sensitive display, wherein the SPL dose is output responsive to user input through the touch-sensitive display.

7. The wearable device of claim 1, wherein outputting comprises displaying a visual message that includes the SPL dose on the display.

8. The wearable device of claim 1, wherein the at least one processor performs an operation comprising determining that the user has an ear health change based on the SPL dose of the personal sound exposure of the user, wherein, responsive to the ear health change, the SPL dose is output, and the biometric sensor data and the SPL dose are wirelessly transmitted to the electronic device.

9. The wearable device of claim 1, wherein the biometric sensor is in contact with the user.

10. The wearable device of claim 1, wherein outputting the SPL dose comprises at least one of displaying a visual message on the display and playing back an audible message through one or more speakers.

11. The wearable device of claim 10, wherein the wearable device is the wrist-worn device, wherein the at least one processor performs at least one operation comprising receiving a SPL of sound of an audio reproduction by a headset worn by the user, wherein the SPL dose is based on the SPL of the ambient sound and the SPL of the sound of the audio reproduction.

12. The wearable device of claim 1 wherein the biometric sensor measures at least one of blood pressure, blood oxygen content, and heart rate.

13. A method performed by a wearable device while worn by a user, the method comprising:
   receiving a biometric sensor data from a biometric sensor that is a part of the wearable device;
   capturing, using a microphone of the wearable device, an ambient sound of an environment, wherein the biometric sensor data is received and the ambient sound is captured while the wearable device is worn by the user;
   determining a sound pressure level (SPL) of the ambient sound;
   determining a SPL dose of a personal sound exposure of the user based on the SPL of the ambient sound, wherein the SPL dose comprises a percentage of an accumulated SPL dose or a time remaining value before a threshold shift occurs;
   determining that the user has a health change based on the SPL dose;
   responsive to determining that the user has the health change,
      providing a notification to the user that includes the SPL dose; and
      wirelessly transmitting at least one of the SPL dose and the biometric sensor data to an electronic device belonging to a second party,
   wherein the wearable device is at least one of an earphone, a headset having two earphones, a wrist-worn device, or a neck-worn device.

14. The method of claim 13, wherein providing the notification comprises at least one of displaying a visual message on a display and playing back an audible message through one or more speakers.

15. The method of claim 14, wherein the display and the one or more speakers are a part of the wearable device.

16. A method performed by a wearable device, the method comprising:
   receiving biometric sensor data from a biometric sensor of the wearable device;
   capturing, using a microphone of the wearable device, an ambient sound of an environment, wherein the biometric sensor data is received and the ambient sound is captured while the wearable device is worn by a user;
   determining a sound pressure level (SPL) of the ambient sound;
   determining a SPL dose of a personal sound exposure of the user based on the SPL of the ambient sound, wherein the SPL dose comprises a percentage of an accumulated SPL dose or a time remaining value before a threshold shift occurs;

transmitting a first notification that includes the biometric sensor data to an electronic device belonging to a second party; and outputting, by the wearable device, a second notification that includes the SPL dose to the user.

17. The method of claim 16 further comprising receiving a SPL of sound of an audio reproduction, wherein the SPL dose is based on the SPL of the ambient sound and the SPL of the sound of the audio reproduction.

18. The method of claim 16, wherein outputting the second notification comprises at least one of: displaying a visual message that indicates the percentage or the time remaining value on a display of the wearable device and playing back an audible message that indicates the percentage or the time remaining value through one or more speakers of the wearable device.

19. The method of claim 18, wherein the visual message is a first visual message, wherein the method further comprises displaying a second visual message that includes information regarding the biometric sensor data on the display of the wearable device.

20. The method of claim 16, wherein the wearable device is a wrist-worn device.

* * * * *